(12) United States Patent
Enhorning

(10) Patent No.: US 6,189,535 B1
(45) Date of Patent: *Feb. 20, 2001

(54) DEFLATABLE VAGINAL PESSARY

(76) Inventor: Goran E. Enhorning, 21 Oakland Pl., Buffalo, NY (US) 14222

(*) Notice: Under 35 U.S.C. 154(b), the term of this patent shall be extended for 0 days.

This patent is subject to a terminal disclaimer.

(21) Appl. No.: 08/041,841
(22) Filed: Apr. 2, 1993

Related U.S. Application Data

(63) Continuation-in-part of application No. 07/854,331, filed on Mar. 19, 1992, now Pat. No. 5,224,494.

(51) Int. Cl.⁷ ........................................................ A61F 6/06
(52) U.S. Cl. .............................. 128/834; 128/836; 128/837
(58) Field of Search ................................. 128/830–841, 128/DIG. 25, 885; 600/29–31

(56) References Cited

U.S. PATENT DOCUMENTS

| | | |
|---|---|---|
| 2,494,393 | 1/1950 | Lamson . |
| 2,602,444 * | 7/1952 | Stanford .............................. 128/885 |
| 2,638,093 | 5/1953 | Kulick . |
| 3,080,865 | 3/1963 | Vincent . |
| 3,646,929 | 3/1972 | Bonnar . |
| 4,019,498 | 4/1977 | Hawtrey et al. . |
| 4,139,006 * | 2/1979 | Corey ...................................... 600/29 |
| 4,428,365 | 1/1984 | Hakky . |
| 4,920,986 | 5/1990 | Biswas . |
| 5,007,894 * | 4/1991 | Enhorning .............................. 600/31 |

FOREIGN PATENT DOCUMENTS

| | | | |
|---|---|---|---|
| 0152343 * | 7/1953 | (AU) | ..................................... 128/836 |
| 0553467 * | 2/1958 | (CA) | ..................................... 128/836 |
| 0274762 | 1/1987 | (EP) . | |
| 1115727 | 5/1968 | (GB) . | |
| 1115727 * | 5/1969 | (GB) . | |

* cited by examiner

Primary Examiner—Michael A. Brown
(74) Attorney, Agent, or Firm—John C. Thompson

(57) ABSTRACT

The pessary 22, which will alleviate the common female problems of stress incontinence and prolapse, includes an annular hollow body 24 and an air tube 26. The hollow body is ring shaped and is made deflatable. While the body 24 is being inserted into the vagina it is evacuated which diminishes its size and thereby reduces the discomfort associated with insertion. Once in place in the vagina, air is given free access to the hollow device 24 whereby elasticity of the device causes it to expand to its normal shape. When the device 24 is to be removed from the vagina the tube 26, which is preferable coiled and stowed at the center of the ring shaped device 24, is extracted and connected to the hollow needle of a syringe. When the syringe sucks out air, the hollow body 24 diminished in size, which reduces the discomfort associated with its removal.

6 Claims, 1 Drawing Sheet

DEFLATABLE VAGINAL PESSARY

CROSS REFERENCE TO RELATED APPLICATIONS

This application is a continuation-in-part of U.S. patent application Ser. No. 07/854,331 filed Mar. 19, 1992, now U.S. Pat. No. 5,224,494.

FIELD OF THE INVENTION

The present invention relates generally to a deflatable vaginal pessary to control urinary incontinence or a prolapse, and more particularly to a vaginal pessary having a rubber-like hollow body which, when the air pressures inside and outside of the hollow body are the same, has a normal operational size; the pessary also including an elongated air tube that permits the hollow body of the pessary to be transformed into a smaller size when air is actively sucked out of the rubber-like hollow body through the air tube.

BACKGROUND OF THE INVENTION

Relaxation of the pelvic tissue may result in prolapse of either the uterus, bladder, rectum, or intestines; it may result in stress incontinence; or it may result in a combination of the above. Surgery may effectively control the above conditions; but if the patient is very old, or for other reasons is a poor operative risk, a vaginal pessary may be considered. However, in this group of women, the introitus, the inlet to the vagina, may be narrow making it painful to insert the pessary.

Various prolapse devices have been in use for several decades. They are usually made of a solid material and, to ensure that they function adequately, they have to be as large as possible to serve as a mechanical barrier, preventing the organs from being extruded through the introitus. That makes it difficult and painful to insert the device and then remove it for cleaning. To overcome the forgoing problem, an inflatable prolapse device, the "Inflatoball", has been developed by Milex Products, Inc., 5915 Northwest Highway, Chicago, Ill. 60631. The mechanism for deflation and inflation of the "Inflatoball" includes a tube attached to a spherical body, which tube extends to just outside the vagina when the spherical body has been properly inserted. The tube ends with a valve which can be readily opened for deflation. It can also be connected with a pump when inflation is desired.

A vaginal pessary for control of urinary incontinence also needs to be large to perform well. As a consequence, insertion and removal of the incontinence device can be painful. An inflatable pessary for controlling incontinence, particularly stress incontinence, is disclosed in U.S. Pat. No. 5,007,894 issued on Apr. 16, 1991. The device consists of an inflatable oval-shaped body with two projections, the oval-shaped body having a central aperture to allow drainage to migrate from the uterus and out of the vagina. The two projections offer support on each side of the urethra and prevent the device from exerting a direct pressure on the urethra. This pessary, when inflated, with the exception of the two projections used for control of urinary incontinence, is somewhat similar to prior art prolapse devices, in the form of donuts, used for control of vaginal prolapse.

Other prior art pessaries that have inflatable portions are shown in U.S. Pat. Nos. 2,638,093, 3,646,929, 4,019,490 and 4,920,986, British Patent 1,115,727, Australian Patent Application 152,363 and European Patent Application 0 274 762. All of these devices, as well as other prior art inflatable devices, have the disadvantage in that air may leak from within the inflatable body, thus reducing its effectiveness.

Another prior art prolapse device is shown in U.S. Pat. No. 4,019,498. This device may be made from an open cell resilient foam material and has the shape of a mushroom. Thus, this device differs from the prior art referred to above because it is a compressible device. When inserted, the head of the mushroom-shaped device will bear against the anterior wall of the vagina at a location adjacent a mid-portion of the urethra, and the stem of the mushroom-shaped device will rest upon the opposed posterior wall of the vagina. This patent teaches that the device may be compressed prior to insertion within the vagina by inserting it within a flexible, air impervious envelope, and that the air may then be driven out of the device, the envelope then being sealed prior to insertion. After the compressed device has been inserted into the vagina, the compression can be released on the device by piercing the envelope with a needle or scalpel, thus letting air enter the envelope. However, once the device has expanded to its normal size, no means are provided for again compressing the device for removal.

OBJECTS AND SUMMARY OF THE INVENTION

It is an object of the present invention to provide a vaginal pessary which may be easier to insert and to remove for cleaning, which pessary is intended for control of urinary incontinence and/or prolapse of the uterus, bladder, rectum, and intestines, and which vaginal pessary does not give the wearer the discomfort of prior art vaginal pessaries.

More specifically, it is an object of the present invention to provide a vaginal pessary which has a hollow body that may be deflated by reducing the air pressure within it below ambient air pressure, making it possible to insert the hollow body into the vagina when deflated, the hollow body resuming its normal operational size when inserted in the vagina by letting ambient air into the hollow body.

In summary, a vaginal pessary is provided which includes a hollow body and an air tube, preferably coiled, which is operatively connected to the hollow body. The volume of the hollow body may be reduced from its normal operational size for relatively easy insertion and removal. The hollow body is preferably formed of a rubber-like material which will have a normal operational size when the air pressure within the hollow body is the same as the air pressure outside of the hollow body. The size of the hollow body may be reduced by withdrawing air from it, and to do this a syringe is connected to the free end of the elongated coiled air tube. After either insertion or removal, the hollow body is permitted to expand to its normal operational size by letting air flow back into it, the resilient material of the hollow body returning it to its normal operational size.

The foregoing will become more apparent after a consideration of the following detailed description taken in conjunction with the accompanying drawings in which a preferred embodiment of this invention is illustrated.

DETAILED DESCRIPTION OF THE PREFERRED EMBODIMENT

The preferred embodiment of the vaginal pessary of the present invention is used for controlling urinary incontinence in women. The pessary includes a hollow body which is completely inserted into the vagina for supporting the tissue of the vaginal wall on each side of the upper urethra so that, when the intra-abdominal pressure is suddenly increased, the vaginal tissue between the points of support will be stretched like a hammock and the tissue will offer counter pressure. This will allow intra-abdominal pressure to be transmitted to the upper urethra so that the closure pressure, i. e., the pressure difference between intra-urethral pressure and simultaneous bladder pressure, will remain positive regardless of the changes in the intra-abdominal pressure, and continence will be preserved. The support afforded to each side of the urethra allows the tissue between the points of support to function like a hammock, so that the tissue will offer counter pressure to sudden increases in intra-abdominal pressure which occurs during coughing, sneezing, laughing and physical exercise. Thus, the urethra will be totally affected by increases in intra-abdominal pressure and retain a pressure greater than in the bladder, such that the closure pressure will remain positive and continence will be preserved.

Figure 1:
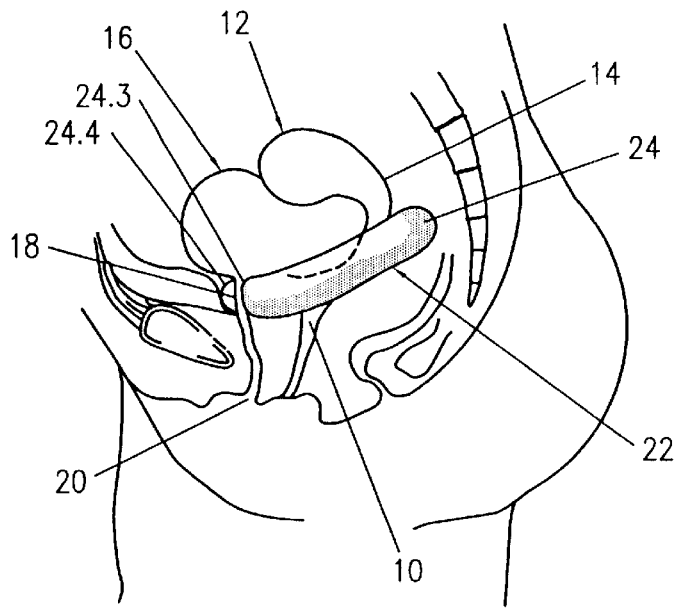
FIG. 1 is a sagittal section of the female pelvis illustrating a preferred form of the deflatable vaginal pessary of this invention positioned within a vagina, the body of the pessary being shown in its normal operational size.

FIG. 1 shows a sagittal section of the female pelvic organs which contact the hollow body portion of the pessary of the present invention. The organs of interest include the vagina 10, the uterus 12, the cervix 14, the bladder 16 and the urethra 18. Bladder 16 stores the urine and passes it through the urethra to the urethral opening 20 for discharge. When intra-abdominal pressure is suddenly raised due to an activity such as coughing, sneezing, laughing or physical exercise; pressure in the bladder 16 is totally affected by this pressure increment. In women who suffer from stress incontinence, the increased intra-abdominal pressure is only incompletely transmitted to the urethra and, at the peak of the stress situation, pressure is no longer higher in the urethra 18 than in the bladder 16, as it normally should be. Consequently there is nothing to prevent the urine from being extruded out through the urethral opening 20. The preferred embodiment of the present invention will correct this situation. It will improve transmission of intra-abdominal pressure to the urethra which will then maintain a higher pressure than the pressure in the bladder regardless of changes in intra-abdominal pressure.

Figure 2:
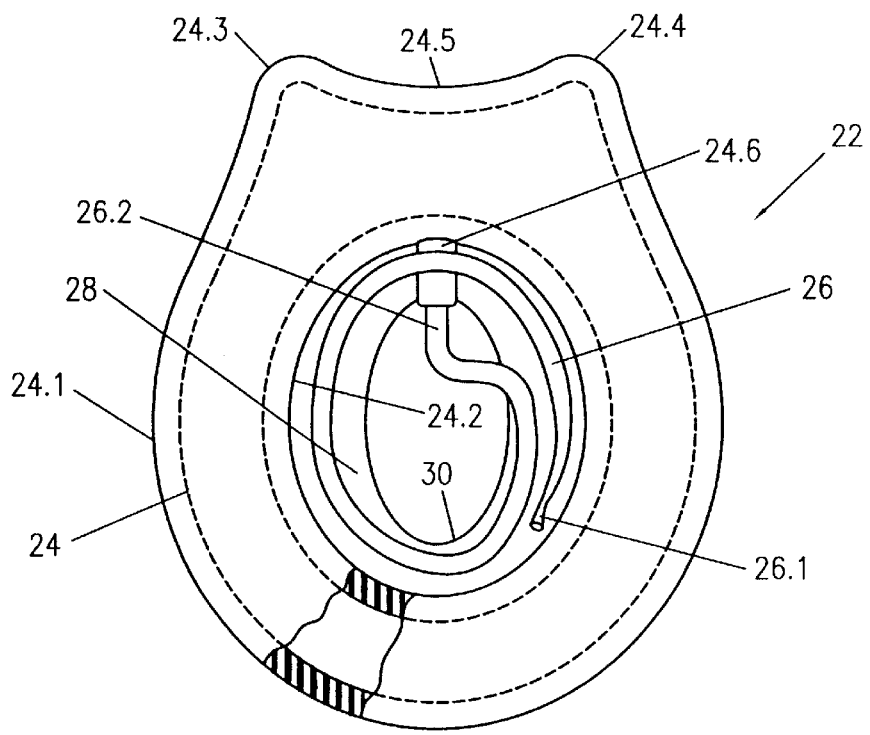
FIG. 2 is a plan view of the vaginal pessary shown in FIG. 1, the pessary including an deflatable donut shaped body section and an elongated air tube, the air tube being shown in its coiled storage position.
Figure 3:
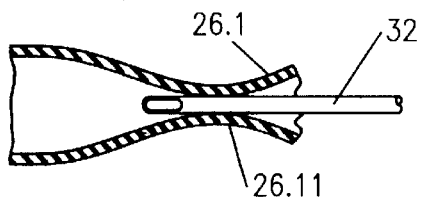
FIG. 3 is an enlarged sectional view showing how the tip of the hollow needle of a syringe may be inserted into the air tube for deflation of the annular body.

With reference primarily to FIG. 2, the preferred embodiment of the present invention is indicated generally at 22 and includes an annular hollow body 24 and an air tube 26. The air tube is used for deflating the hollow body 24 prior to insertion or removal, and will permit air to flow back into the hollow body as the hollow body regains its normal operational size.

The hollow body is generally oval, as seen in FIG. 2, and has an external surface area 24.1, which contacts the walls of the vagina, and an internal surface area 24.2. A diaphragm 28 extends between opposed portions of the interior surface 24.2, the diaphragm having an aperture 30. When the hollow body 24 of the present invention is fully inserted into the vagina in the manner shown in FIG. 1, the air tube 26 will be disposed in a superior position resting upon the diaphragm 28 in the manner illustrated in FIG. 2. The preferred embodiment is of the same shape illustrated in Applicant's copending U.S. patent application Ser. No. 854,331 filed Mar. 19, 1992, the subject matter of which is incorporated herein by reference thereto. It differs from the previous design primarily in that the hollow body is now deflatable rather than inflatable. This means that the hollow body 24 will be transformed into a small size just before it is inserted or just before it is removed by withdrawing air from within the hollow body. After it has been inserted or removed, air is then permitted to flow into the hollow body through the air tube 26 so that the hollow body will then return to its operational normal size. Due to the elasticity of the material that the body section 24 is made from, it will then regain its previous shape. In other words, in the preferred embodiment, the hollow body is hollow as before, but is made of a material which is elastic and therefore can be transformed into a smaller size when one actively sucks air out of the hollow body. When air returns to the hollow body, it will expand again against the resistance which might be offered by the vagina and other tissue surrounding it. The required elasticity is preferably achieved by giving the wall of the hollow body an adequate thickness, as shown in section in FIG. 2. Thus, the body can be made of the same materials which are used for the compressible pumping bulbs as shown in U.S. Pat. No. 2,494,393 at 25, in U.S. Pat. No. 2,638,093 at 28, in U.S. Pat. No. 3,080,865 at 28, or in U.S. Pat. No. 4,428,365 at 9. Alternatively, the hollow body may be made of a relatively thin, non-elastic material that will have the desired shape when filled, and by filling the hollow body with foam material, such as sponge rubber or an open cell foamed polyurethane.

The hollow body illustrated in FIG. 2 includes two projections 24.3 and 24.4, which define between them a U-shaped surface 24.5. When the preferred embodiment of the present invention is positioned in the vagina in the preferred manner shown in FIG. 1, the projections 24.3 and 24.4 will lie to either side of the urethra. These projections will operate to control stress incontinence in females in the same manner as the device shown in applicants prior U.S. Pat. No. 5,007,894.

The air tube 26 is preferably made of a material with a "memory" so that, after being stretched, the tube 26 when slackened will automatically return to its coiled configuration shown in FIG. 2. The free end 26.1 of the air tube is necked down at 26.11 to closely receive the hollow needle 32 of a syringe (not shown) so that air can be withdrawn from the body section through the air tube 26 without substantial leakage past the needle 32. The other end 26.2 of the tube 26 is connected to the stem 24.6 of the body 24 and the end 26.2 is heat sealed within the stem 24.6 in such a manner that air can flow into and out of the hollow interior portion of the body 24. The tube 26 is formed of any suitable material, such as rubber or plastic, a silicone rubber tube to which a "memory" can be imparted being preferred.

Because the preferred embodiment of this invention will have a fixed, although compressible, shape, it will be necessary to provide differing sizes for differing women much in the same manner that a contraceptive diaphragm is provided in differing sizes. It will be necessary for the attending physician to determine the appropriate size for the patient. Thus, in the initial fitting of the hollow body to a patient, the attending physician will select a hollow body of the size that the physician estimates will be suitable for the anatomical dimensions of the particular patient. The hollow body is then deflated, inserted, and then permitted to assume its normal operational size. If it is found that the hollow body is not an appropriate size after it has resumed its normal operational size, another size will be selected.

The hollow body 24 is inserted into a patient much in the same way a contraceptive diaphragm is inserted. However, before insertion, a syringe is connected to the hollow body via the hollow needle 32 and most of the air will be sucked out of the hollow body, thus diminishing the size of the hollow body. It will thus become slim and can be readily inserted. After insertion the hollow needle will be withdrawn permitting air to flow back into the hollow body so that it can expand again against the resistance which might be offered by the vagina. The air tube 26 will be manually manipulated so that it will rest upon the shelf afforded by the diaphragm 28. While the diaphragm may be utilized for maintaining a tube 26 within the vagina after insertion of the hollow body, the tube 26 not having a memory, in the preferred embodiment a tube 26 having a coiled memory is preferred, this being more fully disclosed in Applicant's copending U.S. patent application Ser. No. 07/854,331. Once inserted the pessary used for control of prolapse or stress incontinence should cause no discomfort and it should immediately relieve the patient of her problem. While the pessary can be removed for cleaning every evening, it can also remain inserted for longer periods of time. (Pessaries are often left in the vagina for a month at a time).

When the hollow body is to be deflated for removal, a finger, directed through coiled tube as it rests upon the diaphragm, will pull out the tube for easy attachment to a syringe. To this end, the air tube is approximately 10 inches (25 cm.) long. The hollow needle is then connected to the orifice defined by the necked down portion 26.11, and most of the air is then sucked out. As the size of the hollow body is reduced by sucking the air out of it, relatively easy removal of the body portion from the vagina is possible, and it can now readily be pulled out. While a tube 26 having a necked down portion is illustrated, it should be apparent that the tube 26 may be of uniform diameter and wall thickness, and that an apertured plug may be inserted into the end of the tube to accomplish the same result an the necked down portion 26.11.

While a preferred form of this invention has been described above and shown in the accompanying drawings, it should be understood that the applicant does not intend to be limited to the particular details described above and illustrated in the accompanying drawings, but intends to be limited only to the scope of the invention as defined by the following claims.

What is claimed is:

1. A vaginal pessary which does not give the wearer significant discomfort during use, the volume of the pessary being reducible from its normal operational size for relatively easy insertion and removal, the pessary retaining its normal operational size until it is deflated; said pessary comprising:

a hollow body which may be inserted into the vagina, the hollow body being formed of a material which will expand to its normal operational size when the air pressure within the hollow body is permitted to increase to the same air pressure as that outside of the hollow body, the hollow body having an exterior surface capable of contacting the walls of the vagina when having its normal operational size so that relative movement of the hollow body with respect to the vagina is restricted, and which hollow body may be reduced in size by withdrawing air from the hollow body; and an elongated air tube for permitting air to be withdrawn from the hollow body, the elongated air tube having first and second ends, the tube being of such a length that, when fully extended, the first end of the tube will extend outwardly of the vagina when the hollow body is properly inserted in the vagina, the second end being connected to the hollow body in such a manner that air can flow through the tube to or from the hollow body whereby the air may be withdrawn from the hollow body to reduce its size to permit relatively easy insertion and removal of the hollow body.

2. The vaginal pessary as set forth in claim 1 wherein the first end of the air tube is provided with a reduced diameter portion which will closely engage the hollow needle of a syringe when inserted into the air tube in such a manner that there will not be substantial leakage of air past the needle.

3. The vaginal pessary as set forth in claim 2 wherein the reduced diameter portion is a necked down portion of the air tube.

4. The vaginal pessary as set forth in claim 1 wherein the hollow body has rubber-like walls.

5. The vaginal pessary as set forth in claim 4 wherein the walls of the hollow body are formed of a material having a memory of the normal operational size.

6. The vaginal pessary as set forth in claim 1 wherein the air tube is formed of material having a coiled "memory".

* * * * *